(12) United States Patent
Tabbara et al.

(10) Patent No.: US 6,931,271 B2
(45) Date of Patent: Aug. 16, 2005

(54) SYSTEM FOR ADAPTIVELY DERIVING ECG CHEST LEAD SIGNAL DATA

(75) Inventors: Besher Tabbara, Malden, MA (US); Simon H. Meij, Delft (NL); Stefan P. Nelwan, Rotterdam (NL)

(73) Assignee: Draeger Medical Systems, Inc, Danvers, MA (US)

( * ) Notice: Subject to any disclaimer, the term of this patent is extended or adjusted under 35 U.S.C. 154(b) by 255 days.

(21) Appl. No.: 10/286,020

(22) Filed: Nov. 1, 2002

(65) Prior Publication Data

US 2004/0030257 A1 Feb. 12, 2004

Related U.S. Application Data

(60) Provisional application No. 60/402,791, filed on Aug. 12, 2002.

(51) Int. Cl.$^7$ .................................................. A61B 5/04
(52) U.S. Cl. ...................................................... 600/509
(58) Field of Search ................................. 600/508–513

(56) References Cited

U.S. PATENT DOCUMENTS

| | | | |
|---|---|---|---|
| 4,630,204 A | 12/1986 | Mortara | 600/516 |
| 4,850,370 A | 7/1989 | Dower | 128/699 |
| 5,058,598 A | 10/1991 | Nicklas et al. | 128/699 |
| 5,318,037 A | 6/1994 | Evans et al. | 128/696 |
| 5,377,687 A | 1/1995 | Evans et al. | 128/700 |
| 5,711,304 A | 1/1998 | Dower | 128/696 |
| 6,052,615 A | 4/2000 | Feild et al. | 600/509 |
| 6,119,035 A | 9/2000 | Wang | 600/509 |
| 6,217,525 B1 | 4/2001 | Medema et al. | 600/508 |
| 2002/0045837 A1 | 4/2002 | Wei et al. | 600/509 |
| 2002/0087088 A1 | 7/2002 | Brodnick | 600/509 |

FOREIGN PATENT DOCUMENTS

| | | | |
|---|---|---|---|
| DE | 2348241 | 4/1974 | 4/3 |
| EP | 1 221 299 A2 | 7/2002 | |
| WO | WO01/22876 A1 | 4/2001 | 5/4 |
| WO | WO02/11615 A2 | 2/2002 | |

OTHER PUBLICATIONS

U.S. Appl. No. 10/354,645, filed Jan. 30, 2003, Tabbara et al.
U.S. Appl. No. 09/844,443, filed Mar. 3, 2001, Meij et al.
U.S. Appl. No. 09/922,170, filed Apr. 27, 2001, Meij.

*Primary Examiner*—George Manuel
(74) *Attorney, Agent, or Firm*—Jack Schwartz & Associates

(57) ABSTRACT

A system provides synthesized chest lead signals of a conventional 12 lead electrocardiogram (ECG) signal set. The system adaptively derives ECG chest lead signals for a plurality of the six ECG chest lead signals of a conventional 12 lead ECG signal set. The system includes an input processor for receiving data comprising two measured ECG chest lead signals comprising a particular two of the six ECG chest lead signals of a conventional 12 lead ECG signal set and receiving associated information identifying the particular two signals of the six ECG chest lead signals. A data processor in the system uses the information identifying the particular two signals of the six ECG chest lead signals for identifying and selecting coefficients from a plurality of stored coefficients and applying a transformation using the selected coefficients to the data comprising the two measured ECG chest lead signals to derive data representing a plurality of non-measured ECG chest lead signals. An output processor processes the data representing the plurality of non-measured ECG chest lead signals for output. The selected coefficients are patient non-specific.

13 Claims, 8 Drawing Sheets

FIGURE 3

$$\begin{bmatrix} \text{Derived Chest 1} \\ \text{Derived Chest 2} \\ \text{Derived Chest 3} \\ \text{Derived Chest 4} \end{bmatrix} = \begin{bmatrix} C0,0 & C0,1 & C0,2 & C0,3 \\ C1,0 & C1,1 & C1,2 & C1,3 \\ C2,0 & C2,1 & C2,2 & C2,3 \\ C3,0 & C3,1 & C3,2 & C3,3 \end{bmatrix} * \begin{bmatrix} \text{Lead I} \\ \text{Lead II} \\ \text{Lead V} \\ \text{Lead V+} \end{bmatrix}$$

*Derived Chest 1* = C0,0 * *Lead I* + C0,1 * *Lead II* + C0,2 * *Lead V* + C0,3 * *Lead V+*

*Derived Chest 2* = C1,0 * *Lead I* + C1,1 * *Lead II* + C1,2 * *Lead V* + C1,3 * *Lead V+*

*Derived Chest 3* = C2,0 * *Lead I* + C2,1 * *Lead II* + C2,2 * *Lead V* + C2,3 * *Lead V+*

*Derived Chest 4* = C3,0 * *Lead I* + C3,1 * *Lead II* + C3,2 * *Lead V* + C3,3 * *Lead V+*

Figure 4a

Matrix Coefficients

Coefficient Matrix for lead combination V1V2

{{0.124276, 0.528647, -0.470581, 0.959203},
{0.366777, 0.646839, -0.419272, 0.439137},
{0.243609, 0.612888, -0.240065, 0.063791},
{0.051211, 0.525849, -0.166559, -0.064981}}

Coefficient Matrix for lead combination V1V3

{{0.451028, -0.106476, 1.164328, 0.374929},
{0.173483, 0.300353, -0.362114, 0.614655},
{0.134774, 0.500708, -0.325473, 0.182146},
{0.002947, 0.518251, -0.264215, -0.002567}}

Coefficient Matrix for lead combination V1V4

{{0.604678, -0.029586, 1.479829, 0.243511},
{0.252270, 0.047158, 0.784046, 0.871991},
{-0.086674, 0.241251, -0.280170, 0.536497},
{-0.139528, 0.375958, -0.317945, 0.198076}

Coefficient Matrix for lead combination V1V5

{{0.754809, 0.095972, 1.553465, 0.075997},
{0.706900, 0.320721, 1.087822, 0.555162},
{0.370100, -0.007219, 0.421460, 1.152623},
{-0.172038, 0.150020, -0.183337, 0.589238}}

Coefficient Matrix for lead combination V1V6

{{0.777195, 0.219323, 1.503403, -0.147286},
{0.869673, 0.673735, 1.005209, -0.014885},
{0.707447, 0.291534, 0.474198, 0.809631},
{0.292379, 0.042956, 0.157448, 1.121053}}

Coefficient Matrix for lead combination V2V1

Coefficient Matrix for lead combination V2V3

{{-0.464470, -0.075641, 0.599723, -0.094743},
{0.320585, 0.282038, -0.288053, 0.711130},
{0.270397, 0.491627, -0.247459, 0.258820},
{0.116903, 0.519243, -0.187913, 0.048300}}

Coefficient Matrix for lead combination V2V4

{{-0.448599, -0.070791, 0.551284, -0.086612},
{-0.061269, 0.078345, 0.551089, 0.729656},
{0.027627, 0.235239, -0.189888, 0.582952},
{-0.006967, 0.375606, -0.206621, 0.245240}}

Coefficient Matrix for lead combination V2V5

{{-0.463263, -0.069138, 0.526381, -0.096909},
{0.170326, 0.256123, 0.741823, 0.518945},
{0.161941, -0.032158, 0.288818, 1.139168},
{-0.083482, 0.161517, -0.115293, 0.599321}}

Coefficient Matrix for lead combination V2V6

{{-0.481182, -0.061058, 0.512799, -0.128770},
{0.333948, 0.488976, 0.737081, 0.185473},
{0.452568, 0.199263, 0.356895, 0.917815},
{0.209198, 0.015749, 0.112339, 1.147806}}

Coefficient Matrix for lead combination V3V1

{{0.451028, -0.106476, 0.374929, 1.164328},
{0.173483, 0.300353, 0.614655, -0.362114},
{0.134774, 0.500708, 0.182146, -0.325473},
{0.002947, 0.518251, -0.002567, -0.264215}}

Coefficient Matrix for lead combination V3V2

{{-0.464470, -0.075641, -0.094743, 0.599723},
{0.320585, 0.282038, 0.711130, -0.288053},
{0.270397, 0.491627, 0.258820, -0.247459},
{0.116903, 0.519243, 0.048300, -0.187913}}

Coefficient Matrix for lead combination V3V4

Coefficient Matrix for lead combination V3V5

$\{\{-0.502252, -0.196114, 0.448307, -0.408821\},$
$\{-0.089912, -0.251821, 0.902233, -0.603456\},$
$\{0.086140, -0.138222, 0.419610, 0.930599\},$
$\{-0.060330, 0.199103, -0.144826, 0.677692\}\}$

Coefficient Matrix for lead combination V3V6

$\{\{-0.546441, -0.104891, 0.366195, -0.558147\},$
$\{-0.164332, -0.151235, 0.787226, -0.770679\},$
$\{0.250726, -0.108707, 0.563376, 0.900174\},$
$\{0.147061, -0.078712, 0.174577, 1.139741\}\}$

Coefficient Matrix for lead combination V4V1

$\{\{0.604678, -0.029586, 0.243511, 1.479829\},$
$\{0.252270, 0.047158, 0.871991, 0.784046\},$
$\{-0.086674, 0.241251, 0.536497, -0.280170\},$
$\{-0.139528, 0.375958, 0.198076, -0.317945\}\}$

Coefficient Matrix for lead combination V4V2

$\{\{-0.448599, -0.070791, -0.086612, 0.551284\},$
$\{-0.061269, 0.078345, 0.729656, 0.551089\},$
$\{0.027627, 0.235239, 0.582952, -0.189888\},$
$\{-0.006967, 0.375606, 0.245240, -0.206621\}\}$

Coefficient Matrix for lead combination V4V3

$\{\{-0.478807, -0.273412, -0.403873, 0.616398\},$
$\{-0.044100, -0.353020, -0.623730, 1.162994\},$
$\{0.008301, 0.264660, 0.826313, -0.337073\},$
$\{-0.020283, 0.418091, 0.475264, -0.334412\}\}$

Coefficient Matrix for lead combination V4V5

$\{\{-0.528643, -0.063602, 0.766770, -1.095094\},$
$\{-0.144672, 0.015245, 1.550726, -1.992338\},$
$\{-0.089780, 0.302724, 1.852411, -1.675843\},$
$\{-0.029554, 0.151155, -0.349946, 1.003786\}\}$

Coefficient Matrix for lead combination V4V6

Coefficient Matrix for lead combination V5V1

{{0.754809, 0.095972, 0.075997, 1.553465},
{0.706900, 0.320721, 0.555162, 1.087822},
{0.370100, -0.007219, 1.152623, 0.421460},
{-0.172038, 0.150020, 0.589238, -0.183337}}

Coefficient Matrix for lead combination V5V2

{{-0.463263, -0.069138, -0.096909, 0.526381},
{0.170326, 0.256123, 0.518945, 0.741823},
{0.161941, -0.032158, 1.139168, 0.288818},
{-0.083482, 0.161517, 0.599321, -0.115293}}

Coefficient Matrix for lead combination V5V3

{{-0.502252, -0.196114, -0.408821, 0.448307},
{-0.089912, -0.251821, -0.603456, 0.902233},
{0.086140, -0.138222, 0.930599, 0.419610},
{-0.060330, 0.199103, 0.677692, -0.144826}}

Coefficient Matrix for lead combination V5V4

{{-0.528643, -0.063602, -1.095094, 0.766770},
{-0.144672, 0.015245, -1.992338, 1.550726},
{-0.089780, 0.302724, -1.675843, 1.852411},
{-0.029554, 0.151155, 1.003786, -0.349946}}

Coefficient Matrix for lead combination V5V6

{{-0.530938, 0.167892, 0.722339, -1.600257},
{-0.121147, 0.438455, 1.510999, -2.969914},
{-0.010904, 0.727218, 2.198549, -3.067394},
{0.040145, 0.233045, 2.106434, -1.678931}}

Coefficient Matrix for lead combination V6V1

{{0.777195, 0.219323, -0.147286, 1.503403},
{0.869673, 0.673735, -0.014885, 1.005209},
{0.707447, 0.291534, 0.809631, 0.474198},
{0.292379, 0.042956, 1.121053, 0.157448}}

Coefficient Matrix for lead combination V6V2

Coefficient Matrix for lead combination V6V3

{{-0.546441, -0.104891, -0.558147, 0.366195},
{-0.164332, -0.151235, -0.770679, 0.787226},
{0.250726, -0.108707, 0.900174, 0.563376},
{0.147061, -0.078712, 1.139741, 0.174577}}

Coefficient Matrix for lead combination V6V4

{{-0.564006, 0.073655, -1.038431, 0.378905},
{-0.213630, 0.224033, -1.811486, 0.836061},
{-0.155770, 0.407584, -1.389274, 1.235699},
{0.038798, -0.067708, 0.838759, 0.366871}}

Coefficient Matrix for lead combination V6V5

{{-0.530938, 0.167892, -1.600257, 0.722339},
{-0.121147, 0.438455, -2.969914, 1.510999},
{-0.010904, 0.727218, -3.067394, 2.198549},
{0.040145, 0.233045, -1.678931, 2.106434}}

SYSTEM FOR ADAPTIVELY DERIVING ECG CHEST LEAD SIGNAL DATA

This is a non-provisional application of provisional application Ser. No. 60/402,791 by B. Tabbara et al. filed Aug. 12, 2002.

FIELD OF THE INVENTION

The present invention relates to electrocardiogram (ECG) systems, and in particular to ECG systems which can provide synthesized signals corresponding to, and substituting for, signals provided from electrodes attached to standard body chest positions employed in a conventional 12 lead ECG signal set.

BACKGROUND OF THE INVENTION

ECG systems are well known, and provide information about the physiological status of a patient's heart to a physician. More specifically, so called conventional 12 lead ECG systems exist which provide twelve waveforms, called leads (lead signals), to a physician. To provide such a 12 lead ECG, ten electrodes are placed on the patient's body, and the signals from these electrodes are processed to provide twelve lead signals in a known manner. These ten electrodes include four electrodes which provide signals that are processed to generate six limb lead signals, and six electrodes which provide signals that are processed to provide precordial or chest leads.

However, there are conditions under which it is preferable or expedient to attach a limited number, (e.g. two), chest lead electrodes to a patient and to synthesize (predict) the remaining (e.g., four) chest lead signals of the six chest lead signals of the 12 lead ECG set. Such conditions include, for example, when one or more of the six standard chest lead locations on the patient's body, at which one or more of the electrodes should be placed, may be unavailable due to injury or surgery. Alternatively, it may be desirable to save time (e.g., in an emergency) to attach just two of the six standard chest lead electrodes or there may be one or more chest lead signals giving intermittent or degraded response for which it may be desirable to substitute synthesized signals. In some cases, patient comfort or the use of telemetered ECG signals may render it desirable to monitor patients with a reduced number of chest electrodes, while producing a full set of six chest lead signals. It is desirable under these conditions to still provide the full set of 6 chest lead signals by synthesizing the remaining chest lead signals of the 12 lead ECG set.

It is known that the signals representing the respective ECG lead signals contain mutually redundant information. It is also known that, should one electrode be missing or malfunctioning, an appropriate combination of signals from the other electrodes and/or the other leads, which are available and functional, may be used to generate a synthesized signal which closely approximates the lead signal derived from the missing or malfunctioning electrode. To apply this technique, at least some portion of a full 12 lead ECG is recorded, during an analysis phase. The recorded signals are then processed to generate a function, which may be applied to the lead signals which are available, to synthesize a lead signal which approximates the lead signal which is missing or distorted beyond use. During a synthesis phase, this function is then applied to the available ECG lead signals. Using this technique, a missing lead may be synthesized. However the technique involves the disadvantages of being relatively complex and time consuming to perform. It is desirable to provide an ECG chest lead signal synthesis system that is capable of relatively quickly and simply synthesizing chest lead signals.

BRIEF SUMMARY OF THE INVENTION

A system provides synthesized chest lead signals of a conventional 12 lead electrocardiogram (ECG) signal set. The system adaptively derives ECG chest lead signals for a plurality of the six ECG chest lead signals of a conventional 12 lead ECG signal set. The system includes an input processor for receiving data comprising two measured ECG chest lead signals comprising a particular two of the six ECG chest lead signals of a conventional 12 lead ECG signal set and receiving associated information identifying the particular two signals of the six ECG chest lead signals. A data processor in the system uses the information identifying the particular two signals of the six ECG chest lead signals for identifying and selecting coefficients from a plurality of stored coefficients and applying a transformation using the selected coefficients to the data comprising the two measured ECG chest lead signals to derive data representing a plurality of non-measured ECG chest lead signals. An output processor processes the data representing the plurality of non-measured ECG chest lead signals for output.

BRIEF DESCRIPTION OF THE DRAWING

In the drawing:

FIG. 3 is a diagram illustrating a transformation for synthesizing ECG chest lead signals, according to principles of the present invention.

FIGS. 4a–4e show patient non-specific coefficients for use in the transformation of FIG. 3, according to principles of the present invention.

DETAILED DESCRIPTION OF THE INVENTION

Figure 1:
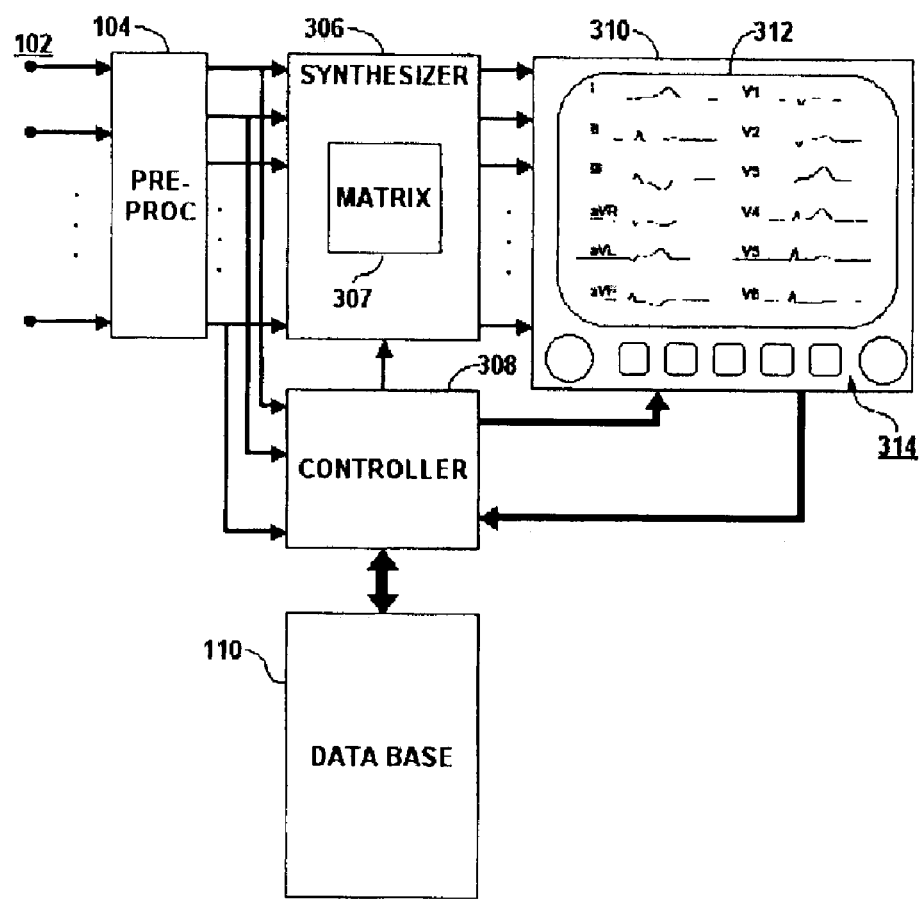
FIG. 1 is a diagram showing an ECG synthesis system in a patient monitoring device, according to principles of the present invention.

FIG. 1 is a diagram showing an ECG synthesis system in a patient monitoring device. In FIG. 1, a plurality 102 of electrodes are intended to be attached to respective locations on a patient's body. The plurality 102 of electrodes are coupled to respective input terminals of a preprocessor 104. Respective output terminals of the preprocessor 104 are coupled to corresponding input terminals of synthesizer 306 and controller 308. Respective output terminals of the synthesizer 306 are coupled to corresponding data input terminals of a display device 310. A synthesizer control output terminal of controller 308 is coupled to a control input terminal of the synthesizer 306, and a display device control output terminal of the controller 308 is coupled to a control input terminal of the display device 310. The display device includes a display screen 312 and a set of user controls 314. These user controls 314 may include, among other controls, knobs, illustrated as circles, and buttons, illustrated as rounded squares. A user control output terminal of the display device 310 is coupled to a user control input terminal of the controller 308. A bidirectional terminal of the controller 308 is coupled to a corresponding terminal of the database 110.

In operation, the plurality of electrodes 102 are ECG electrodes which are intended to be attached to predetermined locations on a patient. In the illustrated embodiment, the plurality of electrodes 102 comprise six electrodes including Left Arm (LA), Right Arm (RA), Left Leg (LL), Right Leg (RL), Chest electrode 1 (lead signal V), and Chest Electrode 2 (lead signal V+). The electrode signals are wirelessly transmitted to preprocessor 104 using known telemetry techniques. In contrast, the conventional 12-Lead ECG set employs 10 electrodes including the four limb electrodes LA, RA, LL, RL and six chest electrodes V1, V2, V3, V4, V5, and V6 and these are used to provide 12 conventional ECG lead signals labeled I, II, III, aVR, aVL, aVF, V1, V2, V3, V4, V5, and V6 as known. Lead signals I and II are computed from LA, RA, LL, and RL electrode raw data and in turn signals I and II are used to mathematically derive III, aAR, aVL, and aVF as known. In the illustrated embodiment, the derivation of the limb lead signals is not germane to the present invention and they are not discussed in the remainder of this application.

The system presented herein advantageously adaptively derives up to four ECG chest lead signals of a conventional 12 lead ECG signal set from two measured ECG chest lead signals coupled to two of the standard chest lead electrode positions (i.e., two of the standard V1, V2, V3, V4, V5, and V6 electrode positions). The system advantageously does this for any patient based on predetermined stored data without requiring the accumulation and analysis of ECG data of a particular patient for use in synthesizing patient specific chest lead signal data. In the FIG. 1 system the six input electrodes 102 comprising signals LA, RA, LL, RL, V (chest electrode 1 lead signal), and V+ (Chest Electrode 2 lead signal) are advantageously used to provide the conventional 12 lead ECG signal set (comprising lead signals identified as I, II, III, aVR, aVL, aVF, V1, V2, V3, V4, V5, and V6).

In the illustrated embodiment of FIG. 1, preprocessor 104 includes analog to digital converters to convert the six input analog electrode signals to multi-bit digital form. Preprocessor 104 further processes the digitized ECG signal data to identify characteristics of each ECG complex and to time align and aggregate (e.g. average, median filter, etc.) some number of successive ECG complexes for each lead, in a known manner. An individual ECG complex comprises signal data occupying a predetermined time period and bandwidth received from a patient attached electrode. Digital data representing the six, optionally averaged, input ECG lead complexes is stored, in a known manner, in respective locations in memory in synthesizer 306. Synthesizer 306, controller 308 and database 110 together process the input ECG lead complexes stored in unit 306 memory to provide data representing ECG waveforms for display on display screen 312 of display device 310.

As illustrated in FIG. 1, the display device 310 displays the 12 lead ECG waveforms from the synthesizer 306 on the display screen 312 in the usual manner for ECG waveforms. In addition, the controller 308 can respond to user input from the user controls 314 on the display device 310, and can condition the display device 310 to display information on the display screen 312. Controller 308 also controls the operation of synthesizer 306 in response to the lead signals from the preprocessor 104, in a manner to be described in detail below. Synthesizer 306 processes the six input electrode signals 102 (LA, RA, LL, RL, V and V+) to provide the conventional 12 lead ECG signal set (I, II, III, aVR, aVL, aVF, V1, V2, V3, V4, V5, and V6) including up to four synthesized chest lead signals, for display on device 310.

The plurality of electrodes 102 are attached to predetermined locations on a patient by a user. Two of the leads (corresponding to leads V and V+) are attached to two of the six chest electrodes located in the six standard positions, V1, V2, V3, V4, V5, and V6 in the conventional 12 lead ECG signal set as previously described. In response to a user selecting two of the six chest electrodes in the standard positions as measurement electrode lead signals V and V+, synthesizer 306 calculates the remaining four chest lead signals. In operation, a user connects the two measurement chest leads V and V+ to chest electrodes at positions V1 and V2 on a patient, for example. The user employs user controls 314 on display device 310 to enter information concerning the monitoring desired, including, e.g., information identifying the patient being measured. The user also employs user controls 314 to select a chest lead identification image window and to associate the two measurement chest leads V and V+ with chest electrodes V1 and V2.

If the user fails to associate the two measurement chest leads V and V+ with any chest electrodes and associated lead labels, the system operates in a passthrough mode. In this mode controller 308 detects that chest leads V and V+ have not been associated with any chest electrodes and conditions the synthesizer 306 to pass the V and V+ lead signals through to the output without change. In this mode synthesizer 306 operation is disabled for the particular patient concerned and synthesizer 306 does not derive any of the remaining four chest lead signals V3, V4, V5, and V6. Instead, the two measurement chest leads V and V+ waveforms and associated V and V+ labels are displayed on screen 312. If the user associates the two measurement chest leads V and V+ with incorrect chest electrodes and associated lead labels, the system may display invalid data.

In normal operation and in response to the user associating the two measurement chest leads V and V+ with correct chest electrodes V1 and V2, synthesizer 306 derives the remaining four chest lead signals V3, V4, V5, and V6. For this purpose controller 308 acquires the user entered information identifying the two measurement chest leads V and V+ as being coupled to chest electrodes V1 and V2. Controller 308 uses this identification information to identify and select coefficients from multiple sets of stored coefficients. The coefficients are advantageously used for any patient and are consequently patient non-specific. This means synthesizer 306 is able to quickly synthesize chest leads without requiring prior time consuming and complicated patient specific data accumulation for use in deriving patient specific transformation data to be used in synthesizing chest lead signals. In contrast, an alternative technique would involve recording at least some portion of a full 12 lead ECG for a particular patient, during an analysis phase. The recorded signals are processed to generate a patient specific function, which may be applied to lead signals which are available, to synthesize a lead signal which approximates a lead signal which is missing or distorted beyond use. During a synthesis phase, this patient specific function is applied to the available ECG lead signals. This alternative technique enables a missing lead to be synthesized for a particular patient but involves the disadvantages of being relatively complex and time consuming to perform.

Controller 308 selects coefficients (in a matrix arrangement, for example) associated with the identified measurement lead assignment (here V=V1 and V+=V2) from database 110. A user is able to associate the two measurement chest leads V and V+ with any two of the six chest electrodes V1–V6 and in any order i.e., V and V+ may be coupled with either V1 and V2 or V2 and V1 respectively. Therefore there are thirty different ways of associating V and V+ with two of the six chest electrodes V1–V6 and there are thirty corresponding sets (e.g., matrices) of coefficients stored in database 110 for use by synthesizer 306 in synthesizing the remaining four chest electrode signals. FIGS. 4a–4e show the thirty sets of patient non-specific coefficients in matrix form for use by synthesizer 306 in synthesizing the remaining four chest electrode signals. The thirty sets of patient non-specific coefficients comprise thirty different, four by four matrices each containing 16 coefficients.

A user is able to relocate either one or both of the two measurement chest leads from V1 and V2 in this exemplary operation description to a different one, or to a different pair, of chest electrodes respectively. As a result the two measurement electrodes are coupled to a selected different pair combination of chest electrodes. The user associates the two measurement chest leads V and V+ with the selected different pair combination of chest electrodes via menus displayed on screen 312 using controls 314. In response, controller 308 dynamically selects from database 110 a coefficient matrix corresponding to the selected different pair combination of electrodes.

Controller 308 retrieves the selected matrix of coefficients associated with the identified measurement lead assignment (here V=V1 and V+=V2) from database 110. Controller 308 inserts the selected matrix coefficients into matrix 307 memory locations in synthesizer 306. Synthesizer 306 employs the selected matrix coefficients 307 to synthesize the remaining four chest lead signals V3, V4, V5, and V6. For this purpose synthesizer 306 uses selected matrix coefficients 307 to perform a matrix multiplication comprising a linear transformation as indicated in FIG. 3. The matrix multiplication performed by synthesizer 306 derives data values representing the remaining four chest lead signals V3, V4, V5, and V6. This is done by multiplying the selected coefficient matrix 307 by an input matrix comprising data values of lead signals I and II (of the conventional 12 lead ECG signal set) as well as data values of the two measurement chest leads V and V+ as shown in FIG. 3. Lead signals I and II are computed from limb electrodes LA, RA, LL, and RL raw data as previously described and known. As indicated in FIG. 3, V3 is computed as:

$$V3 = C0,0 * LeadI + C0,1 * LeadII + C0,2 * LeadV + C0,3 * LeadV+$$

for example. Data values representing chest lead signals V4, V5 and V6 are similarly computed as shown in FIG. 3.

Synthesizer 306 applies the transformation of FIG. 3 to data values of lead signals I and II and V and V+ to derive data values representing V3, V4, V5 and V6. Thereby derived data representing signals V3–V6, together with measurement data representing V1 and V2 (from measurement leads V and V+), is available to provide a waveform display of the full set of chest lead signals V1–V6 on display screen 312 of display device 310. Chest lead signals V1–V6 are displayed on screen 312 together with lead signals I and II as well as signals III, aAR, aVL, and aVF (computed from lead signals I and II as known). As a result screen 312 displays the full conventional 12 lead ECG signal set.

Relocation of either one or both of the two measurement chest leads V and V+ to a selected different pair combination of chest electrodes, together with user association of the two measurement chest leads V and V+ with the selected different pair combination, via screen 312, automatically triggers controller 308 to initiate a fresh synthesis cycle. Specifically, controller 308 automatically selects from database 110 a coefficient matrix corresponding to the selected different pair combination of electrodes (e.g., V2 and V5) for incorporation in location 307 and initiates synthesis by synthesizer 306 of corresponding remaining electrode signals (e.g., V1, V3, V4 and V6) using the transformation of FIG. 3.

Figure 2:
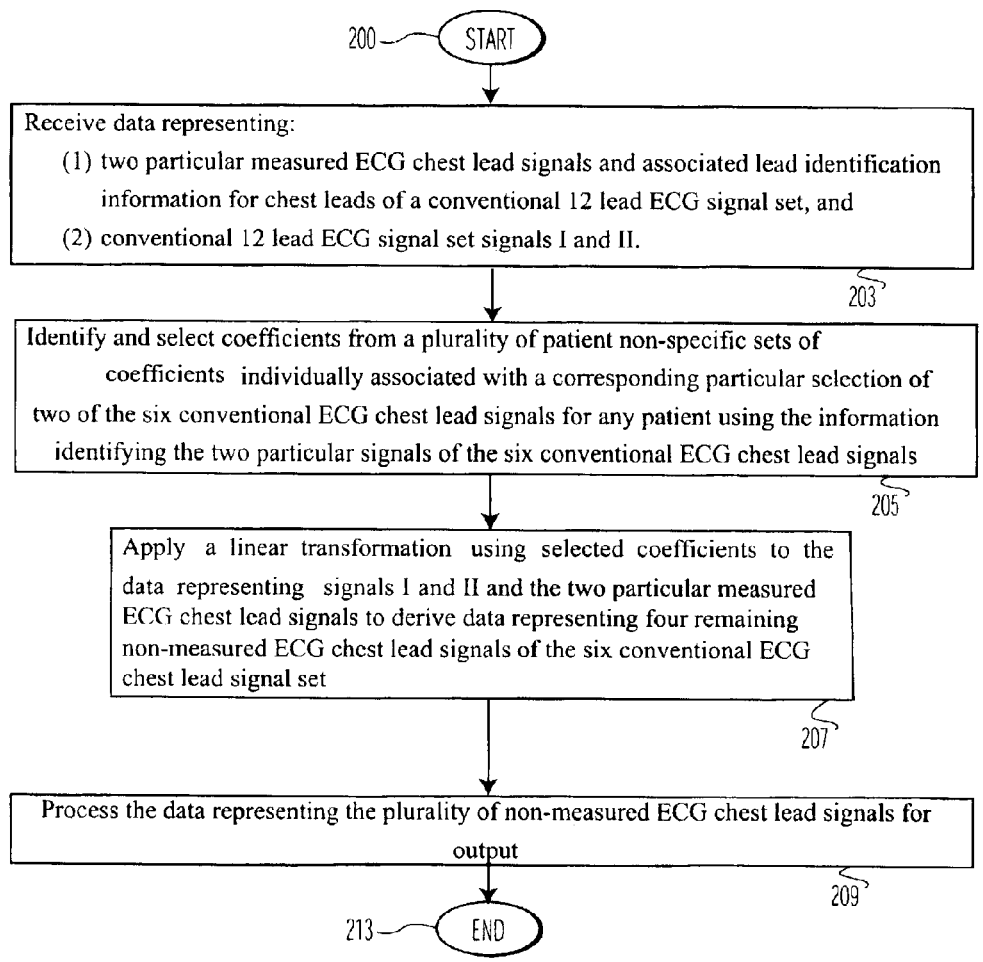
FIG. 2 is a flowchart of a process for adaptively deriving ECG chest lead signals used in the device of FIG. 1, according to principles of the present invention.

FIG. 2 is a flowchart of a process for adaptively deriving ECG chest lead signals used in the system of FIG. 1. After the start at step 200, preprocessor 104 provides synthesizer 306, in step 203, with digital data representing the two measurement chest leads V and V+ and digital data representing lead signals I and II of the conventional 12 lead ECG signal set. In step 205, controller 308 identifies and selects a set of coefficients from a plurality of stored patient non-specific sets of coefficients individually associated with a corresponding particular pair of electrodes. The coefficient sets (matrices in the preferred embodiment) are used for synthesizing (for any patient) up to four of the six ECG chest lead signals of the conventional 12 lead ECG set. Controller 308 selects the set of coefficients associated with the corresponding particular pair of electrodes in response to information identifying the particular two signals of the six conventional ECG chest lead signals entered by a user via user controls 314 (FIG. 1). In step 207 synthesizer 306 applies a transformation using the selected coefficients to digital data representing the two measurement chest lead signals V and V+ and lead signals I and II. This is done to derive data representing the four remaining non-measured ECG chest lead signals of the six ECG chest lead signals of the conventional 12 lead ECG set.

In step 209 controller 308 processes the derived and measured chest lead signal data as well as data representing lead signals I and II and signals III, aAR, aVL, and aVF (computed from lead signals I and II as known) for display on screen 312. Thereby screen 312 of display device 310 displays a full conventional 12 lead ECG signal set. The controller 308 also conditions the display device 310 to display an indication on the display screen 312 to alert the user that four of the displayed ECG chest lead signals are being synthesized. This indication is provided by placing measurement lead signal symbols V and V+ adjacent to the non-synthesized ECG chest waveforms and their associated chest lead signal identification symbols (e.g., symbols V1 and V2). The absence of V and V+ adjacent to the remaining four chest lead signals and identification symbols (e.g., V3, V4, V5 and V6) indicate that these are synthesized waveforms. Alternatively, in other embodiments, synthesized waveforms may be indicated by highlighting the synthesized lead waveforms or the background of the synthesized lead waveforms, in some fashion, such as by varying the intensity or color of the synthesized lead waveforms relative to the other lead waveforms or by displaying a textual identification of the synthesized waveforms on the display screen 312. In another embodiment an alternative indicative symbol may be placed in the vicinity of the synthesized waveforms. The process of FIG. 2 terminates at step 213.

The systems, coefficients and process presented in FIGS. 1–4 are not exclusive. Other systems, coefficients and processes may be derived in accordance with the principles of the invention to accomplish the same objectives. Further, the inventive system as described herein in other embodiments may use a transformation other than a linear transformation which may include a polynomial or trigonometric function, for example. Although this invention has been described with reference to particular embodiments, it will be appreciated that many variations will be resorted to without departing from the spirit and scope of this invention as set forth in the appended claims. For example, the terms "controller" or "synthesizer" as used herein should be broadly construed to include any device capable of receiving, transmitting and/or using information including, without limitation, a processor, microprocessor or similar device, a personal computer, such as a laptop, palm PC, desktop, workstation, or word processor, a network server, a mainframe, an electronic wired or wireless device, such as for example, a telephone, an interactive television, such as for example, a television adapted to be connected to the Internet or an electronic device adapted for use with a television, a cellular telephone, a personal digital assistant, an electronic pager, a digital watch and the like. Further, a controller of the invention may operate in communication with other systems over a communication network, such as, for example, the Internet, an intranet, or an extranet, or may operate as a stand-alone system.

What is claimed is:

1. A system for adaptively deriving ECG chest lead signals for a plurality of the six ECG chest lead signals of a conventional 12 lead ECG signal set, comprising:

an input processor for receiving data comprising two measured ECG chest lead signals comprising a particular two of the six ECG chest lead signals of a conventional 12 lead ECG signal set and receiving associated information identifying said particular two signals of said six ECG chest lead signals;

a data processor for using said information identifying said particular two signals of said six ECG chest lead signals for identifying and selecting coefficients from a plurality of stored coefficients, and applying a transformation using said selected coefficients to said data comprising said two measured ECG chest lead signals to derive data representing a plurality of non-measured ECG chest lead signals; and an output processor for processing said data representing said plurality of non-measured ECG chest lead signals for output.

2. A system according to claim 1 wherein said input processor also receives data representing conventional 12 lead ECG signal set signals I and II, and said data processor applies said transformation using said selected coefficients to said signals I and II in deriving said data representing a plurality of non-measured remaining ECG chest lead signals.

3. A system according to claim 1 wherein said plurality of non-measured ECG chest lead signals comprises the four remaining non-measured ECG chest lead signals of said six conventional ECG chest lead signals.

4. A system according to claim 1 wherein said plurality of stored coefficients comprises a plurality of sets of coefficients and an individual set of coefficients is associated with a corresponding particular selection of two of the six conventional ECG chest lead signals.

5. A system according to claim 4 wherein said plurality of sets of coefficients comprises thirty sets of coefficients associated with thirty available ways of selecting two of the six conventional ECG chest lead signals.

6. A system according to claim 5 wherein said plurality of sets of coefficients comprises thirty coefficient matrices.

7. A system according to claim 1 wherein said data processor identifies and selects coefficients using said information identifying the particular two signals of the six conventional ECG chest lead signals for any patient.

8. A system according to claim 1 wherein said transformation is a linear transformation.

9. A system according to claim 8 wherein said selected coefficients comprise a coefficient matrix and said data processor performs a matrix multiplication operation in performing said linear transformation.

10. A system for adaptively deriving ECG chest lead signals for a plurality of the six ECG chest lead signals of a conventional 12 lead ECG signal set, comprising:

an input processor for receiving data comprising two measured ECG chest lead signals comprising a particular two of the six ECG chest lead signals of a conventional 12 lead ECG signal set and receiving associated information identifying said particular two signals of said six ECG chest lead signals;

a data processor for using said information identifying said particular two signals of said six ECG chest lead signals for identifying and selecting patient non-specific coefficients from a plurality of stored coefficients, and applying a linear transformation using said selected coefficients to said data comprising said two measured ECG chest lead signals to derive data representing a plurality of non-measured ECG chest lead signals; and an output processor for processing said data representing said plurality of non measured ECG chest lead signals for output.

11. A system according to claim 10 wherein said selected patient non-specific coefficients comprise a coefficient matrix and said data processor performs a matrix multiplication operation in performing said linear transformation.

12. A system according to claim 11 wherein said selected coefficient matrix includes coefficients corresponding to the following values, with a 20% tolerance, {{0.124276, 0.528647, −0.470581, 0.959203},
{0.366777, 0.646839, −0.419272, 0.439137},
{0.243609, 0.612888, −0.240065, 0.063791},
{0.051211, 0.525849, −0.166559, −0.064981}}.

13. A method for adaptively deriving ECG chest lead signals for a plurality of the six ECG chest lead signals of a conventional 12 lead ECG signal set, comprising the steps of:

receiving data comprising two measured ECG chest lead signals comprising a particular two of the six ECG chest lead signals of a conventional 12 lead ECG signal set and receiving associated information identifying said particular two signals of said six ECG chest lead signals;

employing said information identifying said particular two signals of said six ECO chest lead signals for identifying and selecting coefficients from a plurality of stored coefficients;

applying a transformation using said selected coefficients to said data comprising said two measured ECG chest lead signals to derive data representing a plurality of non-measured ECG chest lead signals; and processing said data representing said plurality of non-measured ECG chest lead signals for output.

* * * * *